(12) United States Patent
Toriyama et al.

(10) Patent No.: US 11,179,026 B2
(45) Date of Patent: Nov. 23, 2021

(54) ENDOSCOPE PROCESSOR, ENDOSCOPE AND ENDOSCOPE SYSTEM

(71) Applicant: Olympus Corporation, Hachioji (JP)

(72) Inventors: Seiki Toriyama, Hino (JP); Masahiro Yoshino, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 314 days.

(21) Appl. No.: 16/353,630

(22) Filed: Mar. 14, 2019

(65) Prior Publication Data

US 2019/0208993 A1 Jul. 11, 2019

Related U.S. Application Data

(63) Continuation of application No. PCT/JP2017/036211, filed on Oct. 5, 2017.

(30) Foreign Application Priority Data

Oct. 25, 2016 (JP) .............................. JP2016-208424

(51) Int. Cl.
*A61B 1/00* (2006.01)
*A61B 1/04* (2006.01)
(Continued)

(52) U.S. Cl.
CPC ...... *A61B 1/00126* (2013.01); *A61B 1/00124* (2013.01); *A61B 1/042* (2013.01);
(Continued)

(58) Field of Classification Search
CPC ..... A61B 1/00126; A61B 1/042; A61B 1/045; A61B 1/00124; A61B 1/00172;
(Continued)

(56) References Cited

U.S. PATENT DOCUMENTS

2003/0207607 A1 11/2003 Matsumoto et al.
2005/0208832 A1 9/2005 Litz
(Continued)

FOREIGN PATENT DOCUMENTS

JP H07-267019 A 10/1995
JP 2003-323932 A 11/2003
(Continued)

OTHER PUBLICATIONS

International Search Report and Written Opinion from corresponding International Application No. PCT/JP2017/036211, dated Jan. 9, 2018.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

The disclosed technology is directed to an endoscope processor used in an endoscope system which comprises a receptacle configured to receive a plug of an endoscope. The plug includes an illumination plug terminal, an electric plug terminal, and a light-receiving plug terminal. The receptacle includes an illumination receptacle terminal that is displaceable within a predetermined range in a housing for the receptacle and is to be connected to the illumination plug terminal. An electric receptacle terminal is displaceable within a predetermined range in the housing and is to be connected to the electric plug terminal. A light-receiving receptacle terminal that is arranged between the illumination receptacle terminal and the electric receptacle terminal, is attached relative to the housing and is to be connected to the light-receiving plug terminal.

16 Claims, 8 Drawing Sheets

(51) Int. Cl.
*A61B 1/045* (2006.01)
*A61B 1/07* (2006.01)
*A61B 1/06* (2006.01)

(52) U.S. Cl.
CPC .......... *A61B 1/045* (2013.01); *A61B 1/00172* (2013.01); *A61B 1/0669* (2013.01); *A61B 1/07* (2013.01)

(58) Field of Classification Search
CPC ...... A61B 1/07; A61B 1/0669; G02B 6/3825; G02B 6/3843; G02B 6/3871; G02B 6/3874; G02B 6/3875; G02B 6/3877; G02B 6/4293; G02B 23/26; H01R 12/91; H01R 13/6315
USPC .......................................................... 439/460
See application file for complete search history.

(56) References Cited

U.S. PATENT DOCUMENTS

| | | |
|---|---|---|
| 2005/0238294 A1 | 10/2005 | Nagasaka et al. |
| 2008/0170827 A1 | 7/2008 | Mitamura |
| 2009/0264008 A1 | 10/2009 | Matsuda et al. |
| 2011/0184244 A1* | 7/2011 | Kagaya .............. A61B 1/00128 600/182 |
| 2014/0114131 A1* | 4/2014 | Sakai ................... G02B 26/103 600/182 |
| 2015/0245769 A1* | 9/2015 | Mimura ............... A61B 5/0084 600/477 |
| 2016/0089000 A1* | 3/2016 | Hara ...................... A61B 1/015 600/112 |
| 2016/0111804 A1 | 4/2016 | Saito et al. |
| 2016/0227992 A1 | 8/2016 | Yoshino |
| 2016/0287057 A1* | 10/2016 | Fukushima ........ A61B 1/00114 |
| 2017/0035275 A1 | 2/2017 | Yajima et al. |

FOREIGN PATENT DOCUMENTS

| | | |
|---|---|---|
| JP | 2005-268806 A | 9/2005 |
| JP | 2005-315902 | 11/2005 |
| JP | 2008-051981 | 3/2008 |
| JP | 2009-193917 A | 8/2009 |
| JP | 2009-259682 A | 11/2009 |
| JP | 2011-050667 | 3/2011 |
| JP | 2011-152371 | 8/2011 |
| JP | 2015-206912 | 11/2015 |
| JP | 2016-081669 | 5/2016 |
| WO | 2015190134 | 12/2015 |

* cited by examiner

ENDOSCOPE PROCESSOR, ENDOSCOPE AND ENDOSCOPE SYSTEM

CROSS-REFERENCE TO RELATED APPLICATIONS

This application is a continuation application of PCT Application No. PCT/JP2017/036211 filed on Oct. 5, 2017, which in turn claim priority to the Japanese Patent Application No. 2016-208424 filed on Oct. 25, 2016 in Japan which is hereby incorporated by reference in its entirety.

TECHNICAL FIELD

The disclosed technology relates to an endoscope processor, an endoscope and an endoscope system.

DESCRIPTION OF THE RELATED ART

Connector devices such that optical fibers and signal lines or the like are connected together by fitting a plug in a receptacle are conventionally known. In the connector devices described hereinbefore, a floating structure, for example, is used as a structure for absorbing a misregistration which may occur upon fitting the plug in the receptacle.

Specifically, Japanese Patent Laid-open No. 2008-051981 discloses a configuration example such that the floating structure described hereinbefore is used in a light connector plug to be fitted in a light receptacle for optical communication.

In the medical field, on the other hand, endoscope systems are conventionally known, which include a scanning endoscope and a main console. The scanning endoscope has no solid-state imaging device in an insertion portion to be inserted into a body cavity of a subject under examination or surgery, and the main console is detachably connected to the scanning endoscope. Specifically described, the endoscope systems described hereinbefore are configured, for example, so that illumination light supplied from the main console to illuminate an object existing in the body cavity of the subject is transmitted to the scanning endoscope via an illumination optical fiber, a tip portion of the illumination optical fiber, the tip portion being disposed in the scanning endoscope, is pivoted according to a drive signal, which are supplied from the main console, to two-dimensionally scan the object, return light from the object is received by a light-receiving optical fiber and is transmitted from the scanning endoscope to the main console, and an image of the object is generated based on the return light.

In the endoscope systems described hereinbefore, there is, accordingly, a need to dispose such a connector device as having at least three sets of terminals to connect optical fibers and signal lines or the like. In the connector device described hereinbefore, it is desired to dispose a structure that enables to reduce labor to be required for work relating to the connection of individual terminals including the three sets of terminals described hereinbefore.

With the foregoing circumstances in view, the disclosed technology has as objects thereof the provision of an endoscope processor, an endoscope and an endoscope system, in all of which optical fibers and signal lines or the like can be simply and conveniently connected with the use of floating structures.

BRIEF SUMMARY OF EMBODIMENTS

An endoscope processor according to an aspect of the disclosed technology includes a receptacle to be connected to a plug of an endoscope. The plug includes an illumination plug terminal in which an entering end portion of an illumination fiber that transmits illumination light to illuminate an object is disposed, an electric plug terminal in which an end portion of a signal line that extends from an actuator unit capable of pivoting an emitting end portion of the illumination fiber to displace an illumination point by the illumination light is disposed, and a light-receiving plug terminal in which an emitting end portion of a light-receiving fiber that transmits return light from the object illuminated by the illumination light is disposed. The receptacle includes an illumination receptacle terminal that is displaceable within a predetermined range in a housing as a shell for the receptacle and is to be connected to the illumination plug terminal, an electric receptacle terminal that is displaceable within a predetermined range in the housing and is to be connected to the electric plug terminal, and a light-receiving receptacle terminal that is arranged between the illumination receptacle terminal and the electric receptacle terminal, is fixed relative to the housing, and is to be connected to the light-receiving plug terminal.

An endoscope according to another aspect of the disclosed technology includes a plug to be connected to a receptacle of an endoscope processor. The receptacle includes an illumination receptacle terminal and an electric receptacle terminal, both of the illumination receptacle terminal and the electric receptacle terminal being displaceable within predetermined ranges, respectively, in a housing, and a light-receiving receptacle terminal arranged between the illumination receptacle terminal and the electric receptacle terminal and fixed relative to the housing. The plug includes an illumination plug terminal having a first projecting length from a specified surface of the plug, and to be connected to the illumination receptacle terminal, an electric plug terminal having a second projecting length from the specified surface, and to be connected to the electric receptacle terminal, and a light-receiving plug terminal arranged between the illumination plug terminal and the electric plug terminal, having a third projecting length from the specified surface, the third projecting length being greater than the first projecting length and the second projecting length, and to be connected to the light-receiving receptacle terminal.

An endoscope system according to still another aspect of the disclosed technology includes an endoscope processor including a housing for a receptacle, and a first receptacle terminal, a second receptacle terminal and a third receptacle terminal, the first receptacle terminal, the second receptacle terminal and the third receptacle terminal being all disposed in the housing, and an endoscope including a plug, and a first plug terminal to be connected to the first receptacle terminal, a second plug terminal to be connected to the second receptacle terminal and a third plug terminal to be connected to the third receptacle terminal, the first plug terminal, second plug terminal and third plug terminal being all disposed in the plug. At least one of the first receptacle terminal and the second receptacle terminal is displaceable within a predetermined range in the housing. The third receptacle terminal is arranged between the first receptacle terminal and the second receptacle terminal, and is fixed relative to the housing. The third plug terminal is arranged between the first plug terminal and the second plug terminal.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

With reference to the drawings, a description will hereinafter be made about an embodiment of the disclosed technology.

FIGS. 1 through 10 relate to the embodiment of the disclosed technology.

Figure 1:
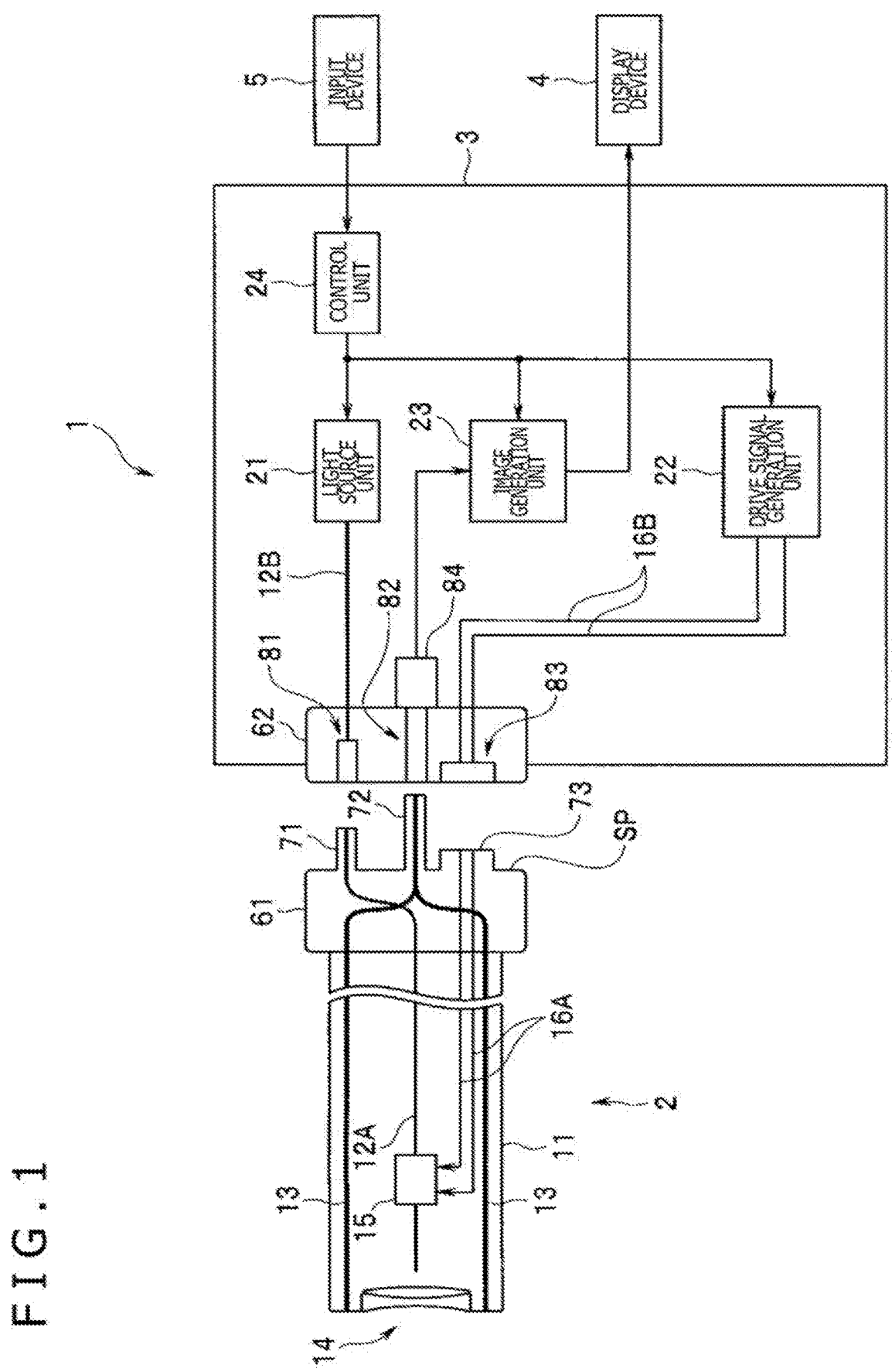
FIG. 1 is a configuration diagram of a main portion of an endoscope system according to an embodiment of the disclosed technology.

As depicted in FIG. 1, an endoscope system 1 includes a scanning endoscope 2 to be inserted into a body cavity of a subject under examination or surgery, a main console 3 to which the endoscope 2 is detachably connectable, a display device 4 to be connected to the main console 3, and an input device 5 enabling to input information and to perform instructions to the main console 3. FIG. 1 is a configuration diagram of a main portion of the endoscope system according to the embodiment.

The endoscope 2 includes an insertion portion 11 formed with an elongated shape that can be inserted into the body cavity of the subject. The endoscope 2 is also configured to scan an object with illumination light supplied from the main console 3.

Inserted in a part inside the insertion portion 11, the part extending from a proximal end portion to a distal end portion of the insertion portion 11, are an illumination fiber 12A and a light-receiving fiber 13. The illumination fiber 12A is an optical fiber for guiding illumination light, which has been supplied from the main console 3, to an observation optical system 14. The light-receiving fiber 13 includes one or more optical fibers for receiving return light from the object and guiding it to the main console 3. Also disposed inside the insertion portion 11 are signal lines 16A for transmitting drive signals, which have been supplied from the main console 3, to an actuator unit 15.

The illumination fiber 12A includes, for example, a single-mode fiber. An entering end portion of the illumination fiber 12A, the entering end portion including a light-entering plane, is arranged inside an illumination plug terminal 71 to be described hereinafter. On the other hand, an emitting end portion of the illumination fiber 12A, the emitting portion including a light-emitting plane, is arranged in a vicinity of a light-entering plane of the observation optical system 14 disposed in the distal end portion of the insertion portion 11.

The light-receiving fiber 13 includes, for example, a plurality of multimode fibers bound together. An entering end portion of the light-receiving fiber 13, the entering end portion including a light-entering plane, is fixedly arranged around a light-emitting plane of the observation optical system 14 in a tip wall of the distal end portion of the insertion portion 11. On the other hand, an emitting end portion of the light-receiving fiber 13, the emitting end portion including a light-emitting plane, is arranged inside a light-receiving plug terminal 72 to be described hereinafter.

The observation optical system 14 includes one or more lenses for collecting light, which has been emitted via the light-emitting plane of the illumination fiber 12A, and irradiating it to the object.

On an intermediate portion of the illumination fiber 12A on the side of the distal end portion of the insertion portion 11, the actuator unit 15 is disposed. This actuator unit 15 is configured so that the emitting end portion of the illumination fiber 12A can be pivoted by driving the emitting end portion based on a drive signal supplied from the main console 3 via one of the signal lines 16A.

The actuator unit 15 includes, for example, a first actuator and a second actuator. The first actuator includes one or more piezoelectric elements that can pivot the emitting end portion of the illumination fiber 12A along a first direction by driving the one or more piezoelectric elements with one or more drive signals supplied from the main console 3. The second actuator includes one or more piezoelectric elements that can pivot the emitting end portion in a second direction, which is orthogonal to the first direction, by driving the one or more piezoelectric elements with one or more drive signals supplied from the main console 3. The actuator unit 15 is, therefore, configured so that an illumination point to be illuminated by illumination light irradiated to the object via the emitting end portion of the illumination fiber 12A, and the observation optical system 14, can be displaced by driving the actuator unit 15 based on one or more drive signals supplied from the main console 3.

On the proximal end portion of the insertion portion 11, a plug 61 is disposed to detachably connect the endoscope 2 to a receptacle 62, which will be described hereinafter, of the main console 3. A connector device in this embodiment includes, therefore, the plug 61 and the receptacle 62.

Figure 2:
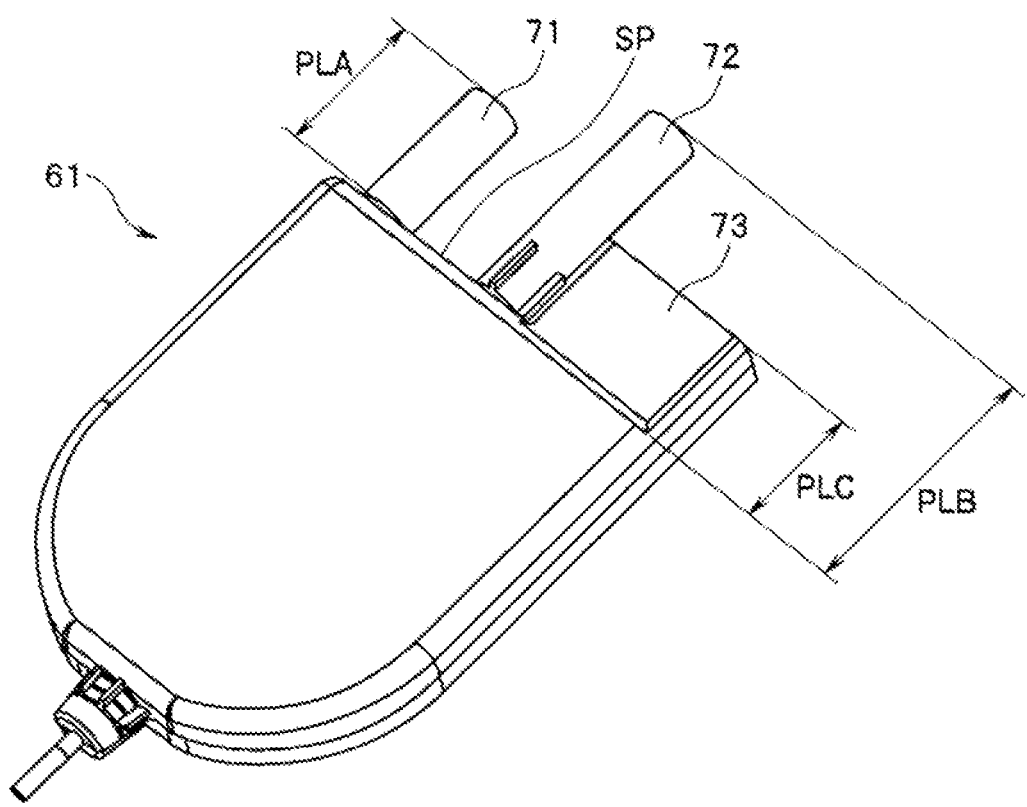
FIG. 2 is a view depicting an example of an external shape of a plug in the embodiment.

The plug 61 is formed, for example, in such an external shape as depicted in FIG. 2. The plug 61 has an illumination plug terminal 71 formed projecting from a specified wall SP located in a direction of connection to the receptacle 62, a light-receiving plug terminal 72 formed projecting from the specified wall SP, and an electric plug terminal 73 formed projecting from the specified wall SP. FIG. 2 is a view depicting an example of the external shape of the plug in the embodiment.

The illumination plug terminal 71 is formed to have a projecting length PLA from the specified wall SP, and is also configured so that it can be connected to a hereinafter-described illumination receptacle terminal 81 disposed in the receptacle 62. The illumination plug terminal 71 is disposed at a location adjacent the light-receiving plug terminal 72 on the specified wall SP. Inside the illumination plug terminal 71, the entering end portion of the illumination fiber 12A is disposed.

The light-receiving plug terminal 72 is formed to have a projecting length PLB from the specified wall SP. The projecting length PLB is greater than the projecting length PLA. The light-receiving plug terminal 72 is also configured so that it can be connected to a hereinafter-described light-receiving receptacle terminal 82 disposed in the receptacle 62. The light-receiving plug terminal 72 is disposed on a central part of the specified wall SP of the plug 61 at a location adjacent the illumination plug terminal 71 and electric plug terminal 73. In other words, the light-receiving plug terminal 72 is arranged between the illumination plug terminal 71 and the electric plug terminal 73. Inside the light-receiving plug terminal 72, an emitting end portion of the light-receiving fiber 13 is disposed.

The electric plug terminal 73 is formed to have a projecting length PLC from the specified wall SP. The projecting length PLC is smaller than the projecting length PLA. The electric plug terminal 73 is also configured so that it can be connected to a hereinafter-described electric receptacle terminal 83 disposed in the receptacle 62. The electric plug terminal 73 is disposed at a location adjacent the light-receiving plug terminal 72 on the specified wall SP. Inside the electric plug terminal 73, end portions of the signal lines 16A extending from the actuator unit 15 are disposed.

The plug 61 is, therefore, formed so that the projecting length PLB of the light-receiving plug terminal 72 becomes longer than the projecting length PLA of the illumination plug terminal 71 and the projecting length PLC of the electric plug terminal 73.

The main console 3 has functions as an endoscope processor. The main console 3 also includes a light source unit 21, a drive signal generation unit 22, an image generation unit 23, and a control unit 24. Further, the receptacle 62 is disposed at a predetermined location of the main console 3 to enable detachable connection of the plug 61 of the endoscope 2 thereto. Also disposed inside the main console 3 are an illumination fiber 12B which is an optical fiber for guiding illumination light, which has been supplied from the light source unit 21, to the illumination receptacle terminal 81 of the receptacle 62, and signal lines 16B for transmitting drive signals, which have been supplied from the drive signal generation unit 22, to the electric receptacle terminal 83 of the receptacle 62.

Figure 3:
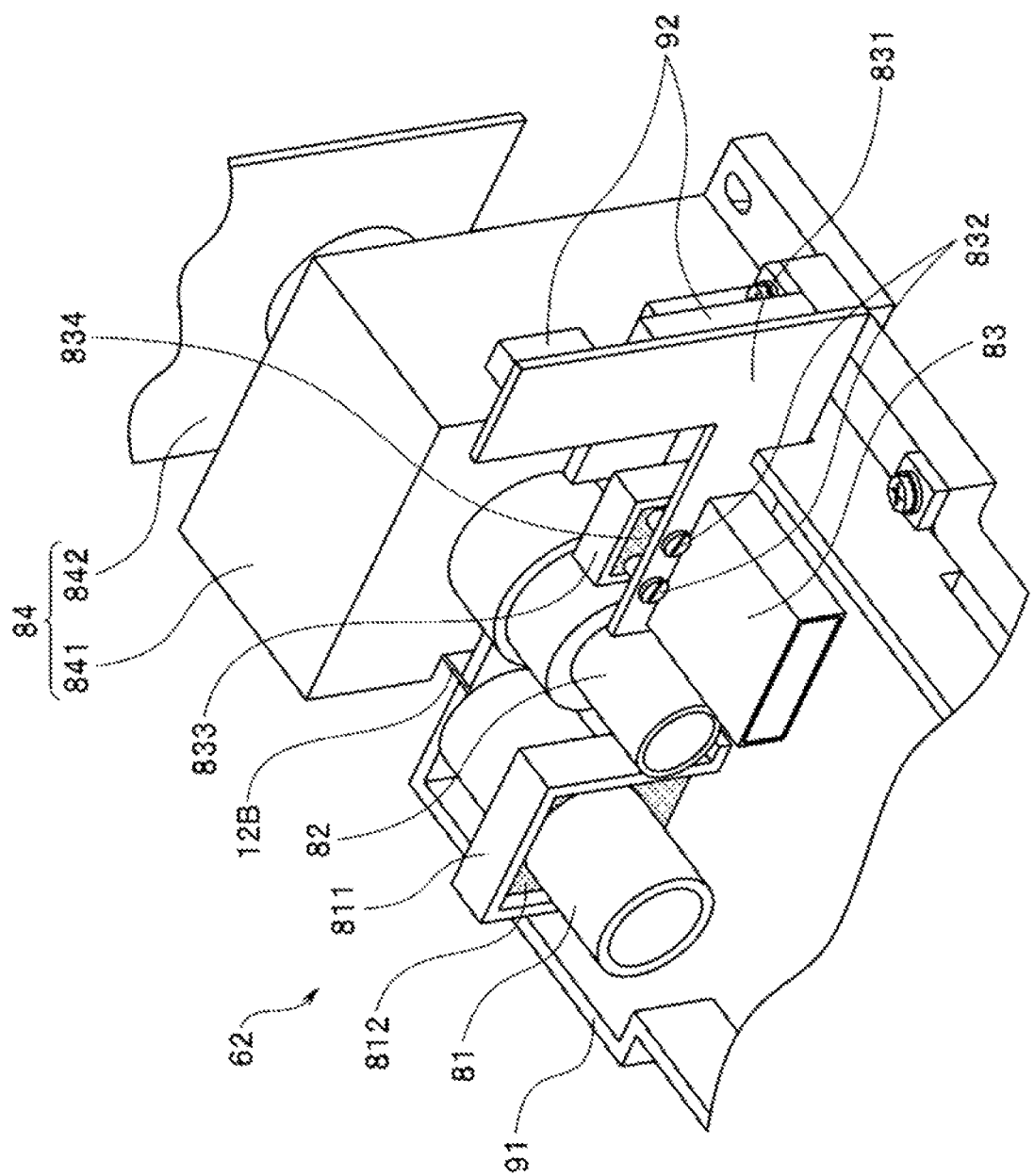
FIG. 3 is a view for describing an example of a configuration of a receptacle in the embodiment.

As depicted in FIG. 3, for example, the receptacle 62 includes the illumination receptacle terminal 81 of a cylindrical shape in which the illumination plug terminal 71 can be inserted and fitted, the light-receiving receptacle terminal 82 of a cylindrical shape in which the light-receiving plug terminal 72 can be inserted and fitted, and the electric receptacle terminal 83 of a rectangular cylindrical shape which can be fitted inside the electric plug terminal 73. At a location adjacent the light-receiving receptacle terminal 82 on a rear end side of the receptacle 62 or a housing 91 to be described hereinafter, a light-receiving unit 84 is disposed. This light-receiving unit 84 is configured to receive return light emitted via the emitting end portion of the light-receiving fiber 13, the emitting end portion being disposed inside the light-receiving plug terminal 72, and also to generate and output an optical detection signal corresponding to the received return signal. FIG. 3 is a view for describing the example of the configuration of the receptacle in the embodiment.

Figure 4:
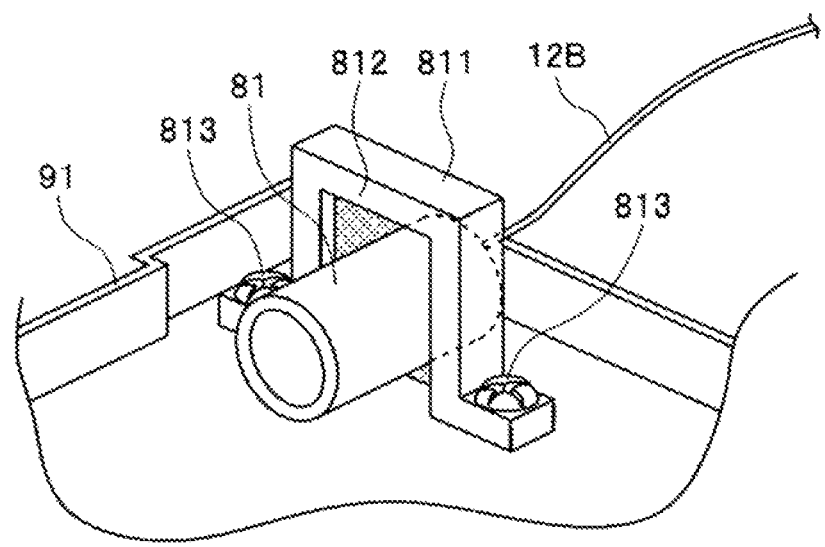
FIG. 4 is a view for describing an example of a configuration of an illumination receptacle terminal in the embodiment.
Figure 5:
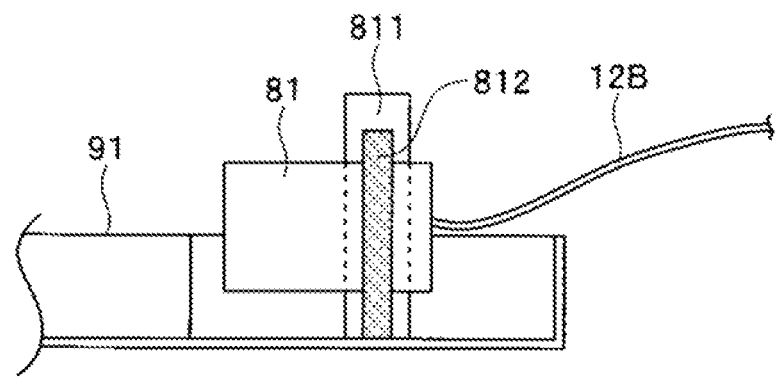
FIG. 5 is a view for describing an example of a configuration of the illumination receptacle terminal in the embodiment.

As depicted in FIG. 3, for example, the illumination receptacle terminal 81 is arranged in a state that it is positioned relative to the housing 91, which forms the shell of the receptacle 62, by a stopper 811 and an elastomer 812. Described specifically, as depicted in FIGS. 4 and 5, the illumination receptacle terminal 81 is arranged in a state that it is, at a portion of an outer peripheral wall thereof, in close circular contact with the elastomer 812 disposed in a space surrounded by the stopper 811, which has an inverted, substantially square U-shaped stopper, and an inner bottom surface of the housing 91. Inside the illumination receptacle terminal 81, an emitting end portion of the illumination fiber 12B, the emitting end portion including a light-emitting plane, is arranged in a state that it is held by a split sleeve 81C to be described hereinafter. FIGS. 4 and 5 are views for describing the example of the configuration of the illumination receptacle terminal in the embodiment.

The stopper 811 is fixed by screws 813 to the inner bottom surface of the housing 91 (see FIG. 4).

According to the configuration as described hereinbefore, a floating structure is, therefore, used for the illumination receptacle terminal 81 so that the illumination receptacle terminal 81 is displaceable within a predetermined range corresponding to elastic force of the elastomer 812 arranged in the space surrounded by the stopper 811 and the housing 91. According to the configuration as described hereinbefore, the illumination receptacle terminal 81 is configured to be displaceable within the predetermined range in the housing 91 and also to be connectable to the illumination plug terminal 71.

As depicted in FIG. 3, for example, the light-receiving receptacle terminal 82 is arranged between the illumination receptacle terminal 81 and the electric receptacle terminal 83, and is also fixed in a state that it is fitted in a notch formed in the housing 91 on a rear end side thereof. Further, the light-receiving receptacle terminal 82 is configured to be connectable to the light-receiving plug terminal 72.

Figure 6:
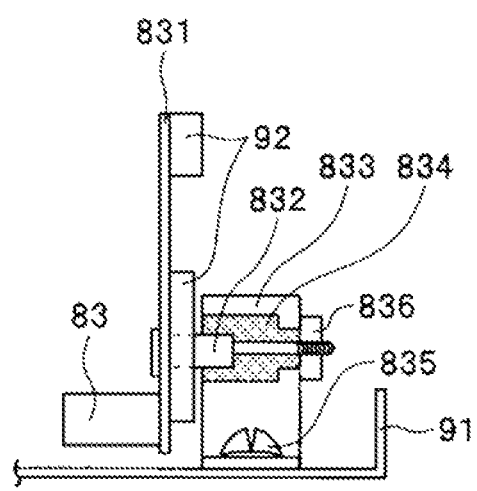
FIG. 6 is a view for describing an example of a configuration of an electric receptacle terminal in the embodiment.

As depicted in FIGS. 3 and 6, for example, the electric receptacle terminal 83 is disposed on a surface of an electric board 831, the surface being on a front end side of the housing 91, in other words, on a front surface of the electric board 831. Furthermore, on a surface of the electric board 831, the surface being on a rear end side of the housing 91, in other words, on a rear surface of the electric board 831, one or more electric connector housings 92 are disposed for use upon connection of the signal lines 16B or the like inside the main console 3, as depicted in FIGS. 3 and 6. FIG. 6 is a view for describing the example of the configuration of the electric receptacle terminal in the embodiment.

As depicted in FIGS. 3 and 6, the electric board 831 is arranged in a state that it is positioned relative to a support member 833, which is disposed on the rear surface of the electric board 831, by a screw member that includes a stepped screw 832 and a nut 836.

The support member 833 is fixed on the inner bottom surface of the housing 91 by screws 835 (see FIG. 6). Further, the support member 833 includes an elastomer 834 around the stepped screw 832.

According to the configuration as described hereinbefore, a floating structure is, therefore, used for the electric receptacle terminal 83 so that the electric receptacle terminal 83 is displaceable together with the electric board 831 within a predetermined range corresponding to elastic force of the elastomer 834 arranged around the stepped screw 832 at the support member 833. According to the configuration as described hereinbefore, the electric receptacle terminal 83 is also configured to be displaceable within the predetermined range in the housing 91 and to be connectable to the electric plug terminal 73.

As depicted in FIG. 3, for example, the light-receiving unit 84 has a light-receiving lens unit 841 and an electric board 842.

The light-receiving lens unit 841 is configured to collect light emitted via the emitting end portion of the light-receiving fiber 13 that is disposed in the light-receiving plug terminal 72 connected to the light-receiving receptacle terminal 82.

The electric board 842 is configured to receive return light emitted via the light-receiving lens unit 841, to generate an optical detection signals corresponding to the received return light, and subsequent to amplification of the generated optical detection signals, to output the amplified optical detection signals to the image generation unit 23.

The light source unit 21 includes, for example, a red laser beam source that emits a laser beam in the red range (hereinafter called "R beam"), a green laser beam source that emits a laser beam in the green range (hereinafter called "G beam"), and a blue laser beam source that emits a laser beam in the blue range (hereinafter called "B beam"). Further, the light source unit 21 is arranged inside the main console 3 at a location remote from the illumination receptacle terminal 81, and is connected to an entering end portion of the illumination fiber 12B, the entering end portion including a light-entering plane. Furthermore, the light source unit 21 is configured so that the output intensities of R beam, G beam and B beam can be changed according to control by the control unit 24. Therefore, the light source unit 21 is configured so that at least one of R beam, G beam and B beam is supplied as illumination light to the illumination fiber 12B according to control by the control unit 24.

The drive signal generation unit 22 includes, for example, a signal generator or the like.

Further, the drive signal generation unit 22 is arranged inside the main console 3 at a position remote from the electric receptacle terminal 83, and is connected to the electric receptacle terminal 83 via the signal lines 16B. Furthermore, the drive signal generation unit 22 is configured, according to control by the control unit 24, to generate at least one drive signal to pivot the emitting end portion of the illumination fiber 12A and then to supply the drive signal to a corresponding one of the signal lines 16B.

The image generation unit 23 includes, for example, an image generation circuitry or the like. The image generation unit 23 is configured to generate an observed image by conducting mapping processing, in which according to control by the control unit 24, optical detection signals sequentially outputted from the light-receiving unit 84 are converted to pixel information such as luminance values and the pixel information is then mapped, and then to output the generated observed image to the display device 4.

The control unit 24 includes, for example, a control circuitry or the like. The control unit 24 is also configured to perform control on each of the light source unit 21, drive signal generation unit 22 and image generation unit 23. Described specifically, the control unit 24 is configured to perform control on the light source unit 21, for example, to repeatedly supply R beam, G beam and B beam in this order to the illumination fiber 12B. The control unit 24 is also configured to perform control on the drive signal generation unit 22 to generate drive signals, for example, such that the emitting end portion of the illumination fiber 12A is pivoted in a spiral scanning pattern. The control unit 24 is also configured to perform control on the image generation unit 23, for example, to generate an observed image by using optical detection signals outputted from the light-receiving unit 84 in a period during which the illumination point of light illuminated on the object moves from a central point to an outermost point of the spiral scanning pattern. The control unit 24 is also configured, for example, to enable detection of a connected state between the electric plug terminal 73 and the electric receptacle terminal 83 via an undepicted signal line. The control unit 24 is also configured, for example, to perform control for the emission of illumination light from the light source unit 21 if the electric plug terminal 73 and the electric receptacle terminal 83 have been detected to be connected together but to perform control for the emission of no illumination light from the light source unit 21 if the electric plug terminal 73 and the electric receptacle terminal 83 have not been detected to be connected together.

The display device 4 includes, for example, a liquid crystal display (LCD), and is configured to enable display of the observed image outputted from the main console 3.

The input device 5 includes one or more switches and/or buttons or the like, which can make one or more instructions to the control unit 24 according to operation by the user. It is to be noted that the input device 5 may be configured as a device discrete from the main console 3 or may be configured as an interface integrated with the main console 3.

Figure 7:
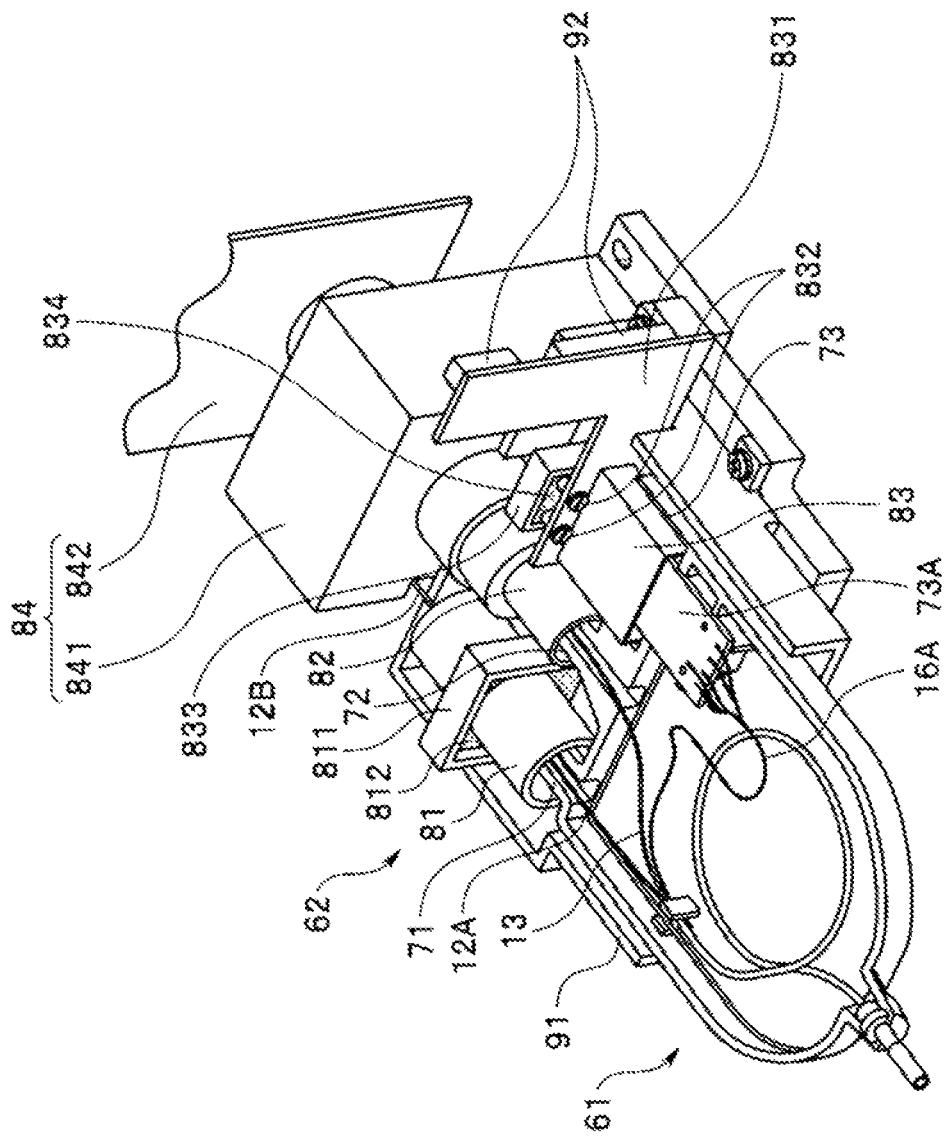
FIG. 7 is a view depicting an example of connection between the plug and the receptacle in the embodiment.

A description will next be made about a specific example of an internal structure of a connecting part between the plug 61 and the receptacle 62. Hereinafter, the description will be made by taking, as an example, a case that the plug 61 and the receptacle 62 are connected in a state of connection as depicted in FIG. 7. FIG. 7 is a view depicting the example of connection between the plug and the receptacle in the embodiment.

Figure 8:
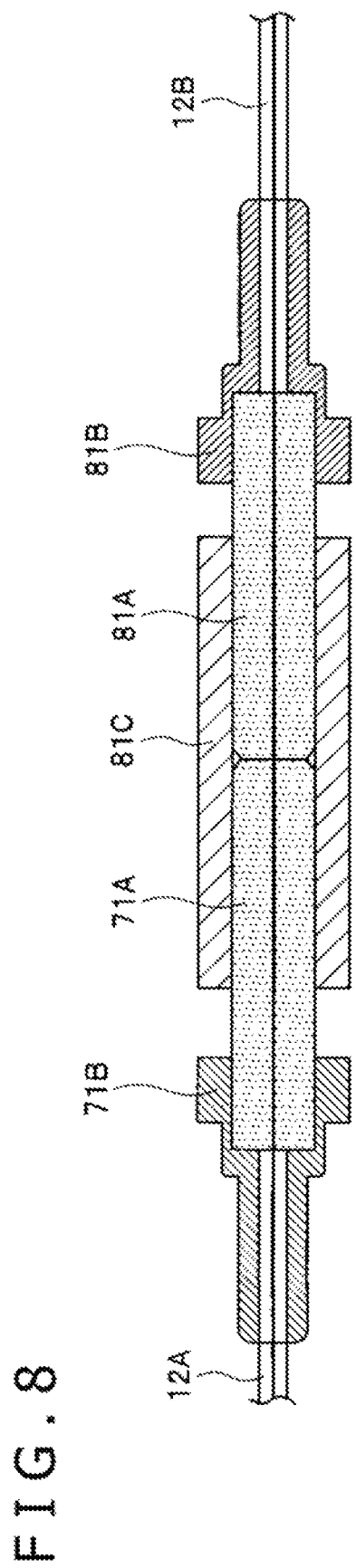
FIG. 8 is a view for describing an example of an internal structure of a connecting part between an illumination plug terminal and the illumination receptacle terminal in the embodiment.

As depicted in FIG. 8, disposed inside the illumination plug terminal 71 are a ferrule 71A for fixing the entering end portion of the illumination fiber 12A, and a ferrule holder 71B for holding the ferrule 71A. FIG. 8 is a view for describing the example of the internal structure of the connecting part between the illumination plug terminal and the illumination receptacle terminal in the embodiment.

As depicted in FIG. 8, disposed inside the illumination receptacle terminal 81 are a ferrule 81A for fixing the emitting end portion of the illumination fiber 12B, and a ferrule holder 81B and a split sleeve 81C for holding the ferrule 81A.

According to the configuration as described hereinbefore, when the plug 61 and the receptacle 62 have been connected together, the ferrule 71A and ferrule 81A are linearly aligned inside the split sleeve 81C, whereby the plug 61 and the receptacle 62 are arranged with the entering end portion of the illumination fiber 12A positioned at the emitting end portion of the illumination fiber 12B. According to the configuration as described above, when the plug 61 and the receptacle 62 have been connected together, the ferrule 71A and the ferrule 81A are in contact with each other at end faces thereof inside the split sleeve 81C, whereby the entering end portion of the illumination fiber 12A and the emitting end portion of the illumination fiber 12B are optically connected together.

Figure 9:
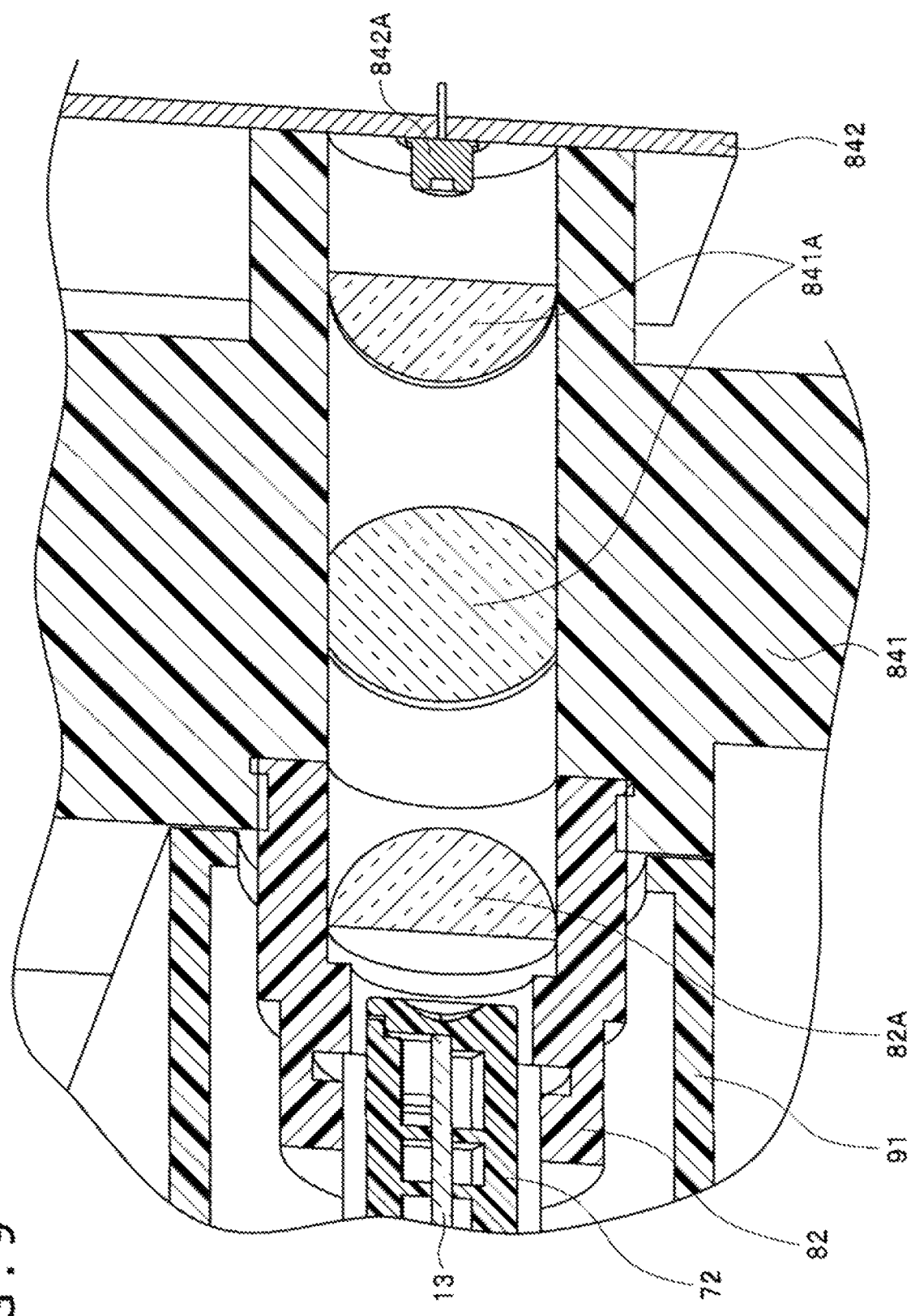
FIG. 9 is a view for describing an example of an internal structure of a connecting part between a light-receiving plug terminal and a light-receiving receptacle terminal in the embodiment.

As depicted in FIG. 9, disposed inside the light-receiving receptacle terminal 82 is a lens 82A for allowing light, which has been emitted via the emitting end portion of the light-receiving fiber 13 disposed inside the light-receiving plug terminal 72, to enter the light-receiving lens unit 841. FIG. 9 is a view for describing an example of an internal structure of a connecting part between the light-receiving plug terminal and the light-receiving receptacle terminal in the embodiment.

As depicted in FIG. 9, disposed inside the light-receiving lens unit 841 is a converging optical system 841A that includes a plurality of lenses.

The converging optical system 841A is arranged in a state that it is positioned at a location adjacent (the lens 82A of) the light-receiving receptacle terminal 82 inside the light-receiving lens unit 841, and is configured to collect return light emitted via the lens 82A. In other words, the converging optical system 841A is configured to collect rerun light emitted via the emitting end portion of the light-receiving fiber 13 in the light-receiving plug terminal 72 that is connected to the light-receiving receptacle terminal 82.

The electric board 842 includes, on a surface thereof, a light-receiving device 842A that receives return light outputted via the converging optical system 841A of the light-receiving lens unit 841. The electric board 842 is also configured to generate optical detection signals corresponding to return light received at the light-receiving device 842A, and subsequent to amplification of the generated optical detection signals, to output the amplified optical detection signals to the image generation unit 23.

The light-receiving device 842A is arranged in a state that it is positioned at a location adjacent the converging optical system 841A on the surface of the electric board 842.

According to the configuration as described hereinbefore, when the plug 61 and the receptacle 62 have been connected together, the light-receiving plug terminal 72 is inserted and fitted inside the light-receiving receptacle terminal 82, whereby light emitted via the emitting end portion of the light-receiving fiber 13 can be received at the light-receiving plane of the light-receiving device 842A.

Figure 10:
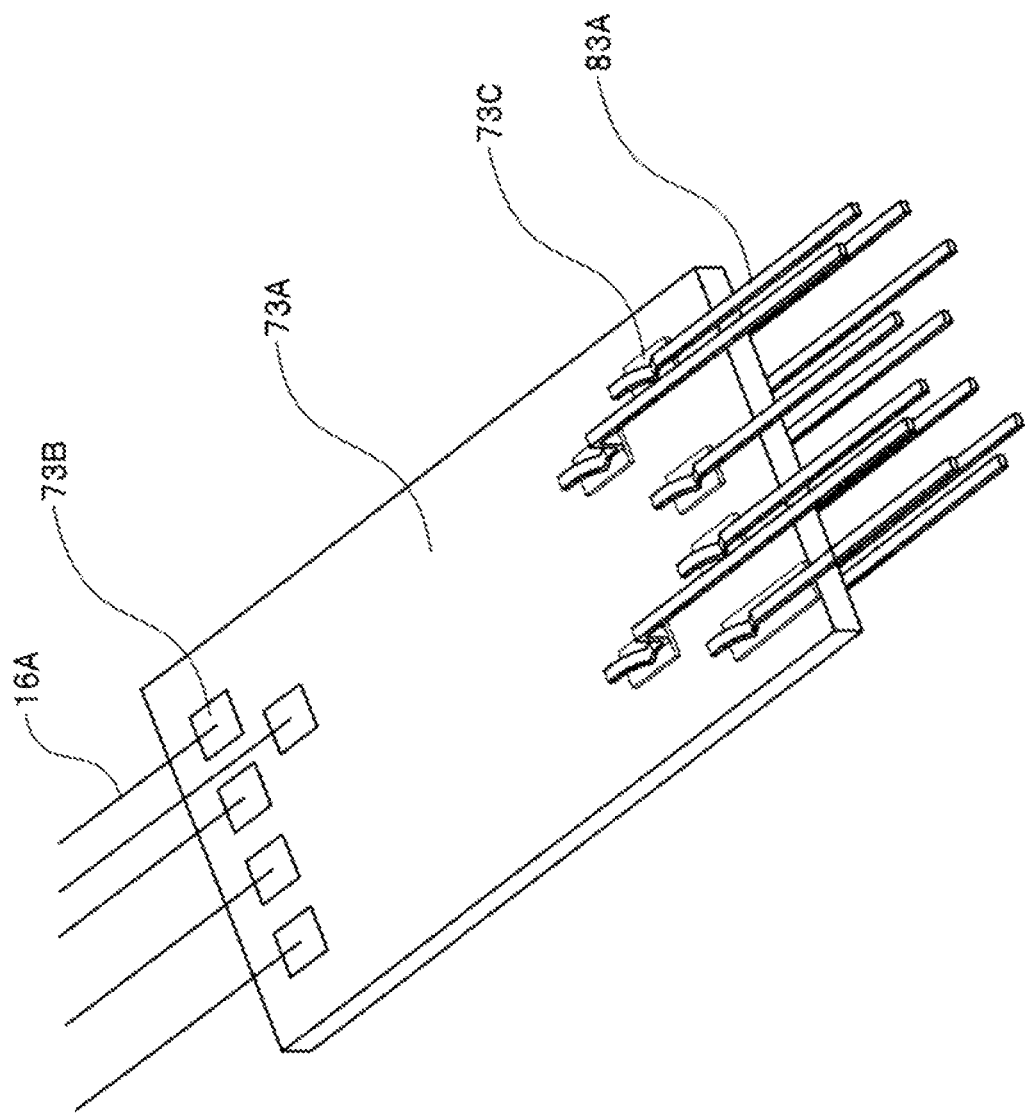
FIG. 10 is a view for describing an example of an internal structure of a connecting part between an electric plug terminal and the electric receptacle terminal in the embodiment.

An electric board 73A is disposed inside the electric plug terminal 73. As depicted in FIG. 10, plug-side lands 73B are formed on the side of an end of the electric board 73A to connect thereto the end portions of the signal lines 16A extending from the actuator unit 15, and receptacle-side lands 73C are formed on the side of an opposite end of the electric board 73A. FIG. 10 is a view for describing the example of the internal structure of the connecting part between the electric plug terminal and the electric receptacle terminal in the embodiment.

As depicted in FIG. 10, disposed inside the electric receptacle terminal 83 are contact pins 83A extending from the front surface of the electric board 831 which is omitted in FIG. 10.

According to the configuration described hereinbefore, when the plug 61 and the receptacle 62 have been connected together, the receptacle-side lands 73C and the contact pins 83A come into contact with each other so that the signal lines 16A and the electric board 831, that is, the signal lines 16B are electrically connected together.

The receptacle 62 also includes the light-receiving unit 84 at a location adjacent the light-receiving receptacle terminal 82 to reduce a loss, which occurs when the light-receiving fiber 13 transmits return light from the object, as much as possible.

However, the configuration of the receptacle 62 as described hereinbefore needs to efficiently receive return light, which has been emitted via the light-receiving fiber 13, at the light-receiving plane of the light-receiving device 842A. This need, therefore, tends to lead to upsizing of the lenses that form the converging optical system 841A. In addition, the configuration of the receptacle 62 as described hereinbefore also needs to output optical detection signals, which have been generated corresponding to the return light received at the light-receiving device 842A, after amplifying them by an amplification circuit such as an amplifier. Therefore, this need also tends to lead to upsizing of the electric board 842 corresponding to the circuit size of the amplification circuit.

If it is desired, for example, to make displaceable the three terminals, that is, the illumination receptacle terminal 81, light-receiving receptacle terminal 82 and electric receptacle terminal 83 in the configuration of the receptacle 62 as described hereinbefore, a need hence arises for disposing a large-scale floating structure that takes into consideration the sum of tolerable misregistrations at the three terminals. As a consequence, a problem arises in that the receptacle 62 is upsized.

In contrast, this embodiment is configured to allow the illumination receptacle terminal 81 and electric receptacle terminal 83 to be independently displaceable inside the housing 91 while preventing displacement of the light-receiving receptacle terminal 82, which is disposed between the illumination receptacle terminal 81 and the electric receptacle terminal 83, by fixing the light-receiving receptacle terminal 82 on the housing 91. Therefore, this embodiment no longer needs to apply floating structures to the upsized converging optical system 841A and electric board 842, respectively, and can dispose floating structures in the housing 91 while individually taking into consideration a tolerable misregistration at the illumination receptacle terminal 81 and a tolerable misregistration at the electric receptacle terminal 83. As a consequence, this embodiment can downsize the receptacle 62.

Further, according to this embodiment, the length, specifically the projecting length PLB of the light-receiving plug terminal 72 disposed between the illumination plug terminal 71 and the electric plug terminal 73 is set greater than the length, specifically the projecting length PLA of the illumination plug terminal 71 and the length, specifically the projecting length PLC of the electric plug terminal 73. Therefore, according to this embodiment, after the light-receiving plug terminal 72 has been connected to, in other words, inserted and fitted in the light-receiving receptacle terminal 82, the illumination plug terminal 71 is provisionally positioned relative to the illumination receptacle terminal 81 and the electric plug terminal 73 is provisionally positioned relative to the electric receptacle plug terminal 83. Further, according to this embodiment, the light-receiving lens unit 841 is fixed on the main console 3 so that the light-receiving receptacle terminal 82, which needs no floating structure, is arranged between the illumination receptacle terminal 81 and the electric receptacle terminal 83. As a consequence, this embodiment can make smaller both of a maximum displacement upon displacement of the illumination receptacle terminal 81 in the housing 91 and a maximum displacement upon displacement of the electric receptacle terminal 83 in the housing 91 compared, for example, with a case in which the light-receiving receptacle terminal 82, the illumination receptacle terminal 81 and the electric receptacle terminal 81 are disposed in this order. In other words, this embodiment can downsize the receptacle 62.

According to this embodiment, the length, specifically the projecting length PLC of the electric plug terminal 73 is set smaller than the length, specifically the projecting length PLA of the illumination plug terminal 71 and the length, specifically the projecting length PLB of the light-receiving plug terminal 72. Therefore, according to this embodiment, after the illumination plug terminal 71 has been connected to the illumination receptacle terminal 81 and the light-receiving plug terminal 72 has also been connected to the light-receiving receptacle terminal 82, the electric plug terminal 73 is connected to the electric receptacle terminal 83. On the other hand, according to this embodiment, control is performed not to allow emission of any illumination light or laser beam from the light source unit 21 if the electric plug terminal 73 and the electric receptacle terminal 83 are not connected together. In other words, according to this embodiment, illumination light or a laser beam is emitted from the light source unit 21 in a state that the illumination plug terminal 71 and the illumination receptacle terminal 81 are completely connected together. According to this embodiment, it is, therefore, possible to safely perform endoscopic observation while avoiding, for example, a situation such that illumination light, specifically a laser beam emitted from the light source unit 21, is discharged to an outside of the main console 3 via the illumination receptacle terminal 81 with the illumination plug terminal 71 not connected thereto.

To obtain advantageous effects as described hereinbefore, it is only necessary for at least the length, specifically the projecting length PLC of the electric plug terminal 73 to be smaller than the length, specifically the projecting length PLA of the illumination plug terminal 71. Similar advantageous effects as those described hereinbefore can, therefore, be obtained even if the plug 61 is configured, for example, so that the length, specifically the projecting length PLC of the electric plug terminal 73 becomes greater than the length, specifically the projecting length PLB of the light-receiving plug terminal 72.

According to this embodiment, the illumination plug terminal 71, the light-receiving plug terminal 72 and electric plug terminal 73 are each disposed projecting from the specified wall SP of the plug 61, and the floating structures are used for the illumination receptacle terminal 81 and electric receptacle terminal 83 of the receptacle 62, respectively. According to this embodiment, the optical fibers and signal lines or the like can, therefore, be simply and conveniently connected together with the use of the floating structures.

This embodiment may also be applied to an endoscope of a system different from the scanning endoscope 2 insofar as it includes a configuration such that three plug terminals and three receptacle terminals are connected together. Described specifically, this embodiment may also be applied substantially similarly, for example, to an endoscope system that includes an endoscope processor, in which a first receptacle terminal, a second receptacle terminal and a third receptacle terminal are disposed in a housing of a receptacle, and an endoscope, in which a first plug terminal to be connected to the first receptacle terminal, a second plug terminal to be connected to the second receptacle terminal and a third plug terminal to be connected to the third receptacle terminal are disposed in a plug. In such an application, it is only necessary, for example, that at least one of the first receptacle terminal and the second receptacle terminal is displaceable within a predetermined range in the housing of the receptacle, the third receptacle terminal is arranged between the first receptacle terminal and the second receptacle terminal and is fixed relative to the housing, and the third plug terminal disposed in the plug is arranged between the first plug terminal and the second plug terminal.

The disclosed technology should not be limited to the embodiment described hereinbefore, and various changes and applications are obviously feasible within a scope not departing from the spirit of the disclosed technology.

In sum, one aspect of the disclosed technology is directed to an endoscope processor used in an endoscope system which comprises a receptacle configured to receive a plug of an endoscope. The plug includes an illumination plug terminal, an electric plug terminal, and a light-receiving plug terminal. The receptacle includes an illumination receptacle terminal that is displaceable within a predetermined range in a housing for the receptacle and is to be connected to the illumination plug terminal. An electric receptacle terminal is displaceable within a predetermined range in the housing and is to be connected to the electric plug terminal. A light-receiving receptacle terminal that is arranged between the illumination receptacle terminal and the electric receptacle terminal, is attached relative to the housing and is to be connected to the light-receiving plug terminal.

The endoscope processor further comprises an optical system arranged adjacent the light-receiving receptacle terminal and configured to collect a return light. A light-receiving device is arranged adjacent the optical system and is configured to receive the return light emitted via the optical system. A light source unit is arranged at a location remote from the illumination receptacle terminal and is configured to supply illumination light to an optical fiber connected to the illumination receptacle terminal. A drive signal generation unit is arranged at a location remote from the electric receptacle terminal and is configured to supply a drive signal to a signal line. The signal line is connected to the electric receptacle terminal to drive an actuator unit. The illumination receptacle terminal is surrounded by an elastomer. The elastomer is supported by a U-shaped stopper and the housing and is configured to be displaceable within a predetermined range corresponding to elastic force of the elastomer. The electric receptacle terminal is disposed on a surface of an electric board. The electric board is attached to an elastomer by a screw member. The elastomer is surrounded by a support member attached to the housing. The electric receptacle terminal is configured to be displaceable within a predetermined range corresponding to elastic force of the elastomer.

Another aspect of the disclosed technology is directed to an endoscope comprises a plug to be connected to a receptacle of an endoscope processor. The receptacle includes an illumination receptacle terminal and an electric receptacle terminal which both of the illumination receptacle terminal and the electric receptacle terminal are displaceable within predetermined ranges in a housing, respectively. A light-receiving receptacle terminal is attached relative to the housing. The plug includes an illumination plug terminal having a first projecting length from a specified surface of the plug and to be connected to the illumination receptacle terminal. An electric plug terminal having a second projecting length from the specified surface and to be connected to the electric receptacle terminal. A light-receiving plug terminal is arranged between the illumination plug terminal and the electric plug terminal having a third projecting length from the specified surface. The third projecting length is greater than the first projecting length and the second projecting length and to be connected to the light-receiving receptacle terminal. The second projecting length is smaller than the first projecting length.

A further aspect of the disclosed technology is directed to an endoscope system comprises an endoscope processor including a housing for a receptacle and a first receptacle terminal, a second receptacle terminal and a third receptacle terminal. The first receptacle terminal, the second receptacle terminal and the third receptacle terminal are all disposed in the housing. An endoscope including a plug and a first plug terminal to be connected to the first receptacle terminal, a second plug terminal to be connected to the second receptacle terminal, and a third plug terminal to be connected to the third receptacle terminal. The first plug terminal, second plug terminal and third plug terminal are all disposed in the plug. At least one of the first receptacle terminal and the second receptacle terminal is displaceable within a predetermined range in the housing. The third receptacle terminal is arranged between the first receptacle terminal and the second receptacle terminal and is attached relative to the housing. The third plug terminal is arranged between the first plug terminal and the second plug terminal.

The first receptacle terminal is an illumination receptacle terminal and is to be connected to the first plug terminal. The second receptacle terminal is an electric receptacle terminal and is to be connected to the second plug terminal. The third receptacle terminal is a light-receiving receptacle terminal and is to be connected to the third plug terminal. The endoscope system further comprises a optical system arranged adjacent the light-receiving receptacle terminal and configured to collect a return light. A light-receiving device is arranged adjacent the optical system and configured to receive the return light emitted via the optical system. The endoscope further comprises a light source unit configured to supply illumination light. An optical fiber is configured to receive the illumination light from the light source and is connected to the illumination receptacle terminal. A signal line is connected to the electric receptacle terminal. A drive signal generation unit is arranged at a location remote from the electric receptacle terminal and is configured to supply a drive signal to the signal line. A stopper is attached relative to the housing. An elastomer is surrounded by the stopper and is configured to support the illumination receptacle terminal so that illumination receptacle terminal is displaceable within the predetermined range in the housing. An electric board includes a surface and is configured to attach the electric receptacle terminal on the surface. A support member is attached relative to the housing. An elastomer surrounded by the support member and is configured to support the electric board so that electric receptacle terminal is displaceable within the predetermined range in the housing. An illumination fiber includes an entering end and an emitting end. The entering end is attached relative to the first plug terminal and the illumination fiber is configured to transmit illumination light to an object. An actuator unit is configured to pivot the emitting end of the illumination fiber. A signal line extends from the actuator unit to the second plug terminal and is configured to transmit a drive signal for driving the actuator unit. A light-receiving fiber includes an emitting end. The emitting end of the light-receiving fiber is attached relative to the third plug terminal. The light-receiving fiber is configured to transmit a return light from the object illuminated by the illumination light. The first plug terminal includes a first projecting length from a specified surface of the plug and to be connected to the first receptacle terminal. The second plug terminal includes a second projecting length from the specified surface and to be connected to the second receptacle terminal. A third plug terminal is arranged between the first plug terminal and the second plug terminal. The third plug terminal includes a third projecting length from the specified surface. The third projecting length is greater than the first projecting length and the second projecting length and to be connected to the third receptacle terminal. The second projecting length is smaller than the first projecting length.

A yet further aspect of the disclosed technology is directed to an endoscope processor used in an endoscope system that comprises a receptacle includes an illumination receptacle terminal, a light-receiving receptacle terminal, an electric receptacle terminal all of which are integrally attached to a housing to define the receptacle. The illumination receptacle terminal, and the electric receptacle terminal are capable of being displaced via floating structures to the housing and the light-receiving receptacle terminal being stably attached to the housing. The receptacle configured to receive a plug of an endoscope having an insertion portion inserted into a body of a subject for examination. The plug includes an illumination plug terminal, a light receiving plug terminal, and an electric plug terminal all of which are integrally attached to the endoscope to define the plug. Each of the illumination plug terminal, the light receiving plug terminal, and the electric plug terminal corresponds to each of the illumination receptacle terminal, the light-receiving receptacle terminal, and the electric receptacle terminal, respectively.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope processor used in an endoscope system comprising:
    a receptacle configured to receive a plug of an endoscope, the plug including an illumination plug terminal, an electric plug terminal, and a light-receiving plug terminal,
    wherein the receptacle includes:
        an illumination receptacle terminal that is displaceable within a predetermined range in a housing for the receptacle and is configured to be connected to the illumination plug terminal,
        an electric receptacle terminal that is displaceable within a predetermined range in the housing and is configured to be connected to the electric plug terminal, and
        a light-receiving receptacle terminal that is fixed relative to the housing, and is configured to be connected to the light-receiving plug terminal,
    wherein the illumination receptacle terminal is at least partially surrounded by an elastomer, the elastomer being supported by a stopper and by the housing such that the illumination receptacle terminal is displaceable within a predetermined range corresponding to an elastic force of the elastomer.

2. The endoscope processor of claim 1, further comprising:
    an optical system comprising at least one lens arranged adjacent the light-receiving receptacle terminal, and configured to collect a return light; and
    a light-receiving device arranged adjacent the optical system, and configured to receive the return light emitted via the optical system.

3. The endoscope processor of claim 1, further comprising:
    a light source arranged at a location remote from the illumination receptacle terminal, and configured to supply illumination light to an optical fiber connected to the illumination receptacle terminal; and
    a signal generator arranged at a location remote from the electric receptacle terminal, and configured to supply a drive signal to a signal line, the signal line being connected to the electric receptacle terminal, to drive an actuator.

4. The endoscope processor of claim 1, wherein the stopper is U-shaped.

5. The endoscope processor of claim 1, wherein
    the electric receptacle terminal is disposed on a surface of an electric board,
    the electric board is attached to an other elastomer by a screw member,
    the other elastomer is at least partially surrounded by a support member attached to the housing, and
    the electric receptacle terminal is configured to be displaceable within a predetermined range corresponding to an elastic force of the other elastomer.

6. The endoscope processor of claim 1, wherein
    the illumination receptacle terminal and the electric receptacle terminal are displaceable within predetermined ranges, respectively, in the housing,
    the illumination plug terminal has a first projecting length from a specified surface of the plug, and is configured to be connected to the illumination receptacle terminal;
    the electric plug terminal has a second projecting length from the specified surface, and is configured to be connected to the electric receptacle terminal; and
    the light-receiving plug terminal arranged between the illumination plug terminal and the electric plug terminal, has a third projecting length from the specified surface, the third projecting length being greater than the first projecting length and the second projecting length, and is configured to be connected to the light-receiving receptacle terminal.

7. The endoscope processor of claim 6, wherein the second projecting length is smaller than the first projecting length.

8. An endoscope system comprising:
    an endoscope processor including a housing for a receptacle, and a first receptacle terminal, a second receptacle terminal and a third receptacle terminal, the first receptacle terminal, the second receptacle terminal and the third receptacle terminal being all disposed in the housing; and
    an endoscope including a plug, and a first plug terminal configured to be connected to the first receptacle terminal, a second plug terminal configured to be connected to the second receptacle terminal and a third plug terminal configured to be connected to the third receptacle terminal, the first plug terminal, second plug terminal and third plug terminal being all disposed in the plug, wherein
    at least one of the first receptacle terminal and the second receptacle terminal is displaceable within a predetermined range in the housing, and
    the third receptacle terminal is fixed relative to the housing,
    wherein the endoscope system further comprises:
        a stopper attached relative to the housing; and
        an elastomer at least partially surrounded by the stopper and configured to support the first receptacle terminal such that first receptacle terminal is displaceable within the predetermined range in the housing.

9. The endoscope system of claim 8, wherein
    the first receptacle terminal is an illumination receptacle terminal and is configured to be connected to the first plug terminal, the second receptacle terminal is an electric receptacle terminal and is configured to be connected to the second plug terminal, and the third receptacle terminal is a light-receiving receptacle terminal and is configured to be connected to the third plug terminal.

10. The endoscope system of claim 9, further comprising:
an optical system comprising at least one lens arranged adjacent the light-receiving receptacle terminal and configured to collect a return light; and
a light-receiving device arranged adjacent the optical system and configured to receive the return light emitted via the optical system.

11. The endoscope system of claim 9, further comprising:
a light source configured to supply illumination light, and
an optical fiber configured to receive the illumination light from the light source and connected to the illumination receptacle terminal.

12. The endoscope system of claim 9, further comprising:
a signal line connected to the electric receptacle terminal, and
a signal generator arranged at a location remote from the electric receptacle terminal, and configured to supply a drive signal to the signal line.

13. The endoscope system of claim 8, further comprising:
an illumination fiber having an entering end and an emitting end, the entering end being attached relative to the first plug terminal, the illumination fiber being configured to transmit illumination light to an object;
an actuator configured to pivot the emitting end of the illumination fiber;
a signal line extending from the actuator to the second plug terminal and configured to transmit a drive signal for driving the actuator; and
a light-receiving fiber having an emitting end, the emitting end of the light-receiving fiber being attached relative to the third plug terminal, the light-receiving fiber being configured to transmit a return light from the object illuminated by the illumination light.

14. The endoscope system of claim 8, wherein
the first plug terminal having a first projecting length from a specified surface of the plug, and configured to be connected to the first receptacle terminal,
the second plug terminal having a second projecting length from the specified surface, and configured to be connected to the second receptacle terminal, and
a third plug terminal arranged between the first plug terminal and the second plug terminal, the third plug terminal having a third projecting length from the specified surface, the third projecting length being greater than the first projecting length and the second projecting length, and configured to be connected to the third receptacle terminal.

15. The endoscope system of claim 14, wherein the second projecting length is smaller than the first projecting length.

16. An endoscope system comprising:
an endoscope processor including a housing for a receptacle, and a first receptacle terminal, a second receptacle terminal and a third receptacle terminal, the first receptacle terminal, the second receptacle terminal and the third receptacle terminal being all disposed in the housing; and
an endoscope including a plug, and a first plug terminal configured to be connected to the first receptacle terminal, a second plug terminal configured to be connected to the second receptacle terminal and a third plug terminal configured to be connected to the third receptacle terminal, the first plug terminal, second plug terminal and third plug terminal being all disposed in the plug, wherein
at least one of the first receptacle terminal and the second receptacle terminal is displaceable within a predetermined range in the housing, and
the third receptacle terminal is fixed relative to the housing,
wherein the endoscope system further comprises:
an electric board having a surface and configured to attach the second receptacle terminal on the surface;
a support member attached relative to the housing; and
an elastomer at least partially surrounded by the support member and configured to support the electric board such that the second receptacle terminal is displaceable within the predetermined range in the housing.

* * * * *